United States Patent [19]

Grenier

[11] Patent Number: 4,724,118
[45] Date of Patent: Feb. 9, 1988

[54] DEVICE FOR DETECTING FISSIONABLE MATERIAL

[75] Inventor: Gérard Grenier, Limeil-Brevannes, France

[73] Assignee: Commissariat a l'Energie Atomique, Paris, France

[21] Appl. No.: 918,727

[22] Filed: Oct. 2, 1986

[30] Foreign Application Priority Data

Oct. 2, 1985 [FR] France .................. 85 14623

[51] Int. Cl.$^4$ .................................. G21G 1/08
[52] U.S. Cl. ............................ 376/159; 376/257; 250/491.1; 250/390
[58] Field of Search ............... 376/159, 257; 250/390 C, 358.1, 390 R, 491.1, 492.1

[56] References Cited

U.S. PATENT DOCUMENTS

| | | | |
|---|---|---|---|
| 2,938,119 | 5/1960 | McKay | 250/390 C |
| 3,018,374 | 1/1962 | Pritchett . | |
| 3,124,679 | 3/1964 | Tittman et al. | 376/159 |
| 3,146,349 | 8/1964 | Jordan | 250/390 C |
| 3,315,077 | 4/1967 | Jones, Jr. et al. | 250/390 C |
| 3,463,922 | 8/1969 | Senftle et al. | 250/363 |
| 3,492,479 | 1/1970 | Lowery et al. | 250/390 C |
| 3,707,631 | 12/1972 | Untermyer . | |
| 3,736,429 | 5/1973 | Foley . | |
| 3,812,364 | 5/1974 | Higatsberger et al. | 250/390 C |
| 3,832,545 | 8/1974 | Bartko | 250/367 |
| 3,942,003 | 3/1976 | Apenberg et al. | 250/390 C |
| 3,997,787 | 12/1976 | Fearon et al. | 250/359.1 |
| 4,024,393 | 5/1977 | Braun et al. | 250/390 C |
| 4,266,132 | 5/1981 | Marshall . | |
| 4,268,754 | 5/1981 | Srapeniants et al. | 250/390 C |
| 4,278,885 | 7/1981 | Alfthan et al. | 250/390 C |
| 4,291,227 | 9/1981 | Caldwell et al. | 250/390 C |
| 4,314,155 | 2/1982 | Sowerby | 250/390 C |

FOREIGN PATENT DOCUMENTS 424039 9/1974 U.S.S.R. .................. 250/390 C

OTHER PUBLICATIONS

Nuclear Instruments & Methods, vol. 141, Mar. 1977, pp. 299-306, North-Holland Publishing Co., K. W. MacMurdo et al.: "Assay of Fissile Materials by a Cyclic Method of Neutron Activation and Delayed-Neutron Counting" *pp. 299-300*.

Kerntechnik, vol. 15, No. 12, Dec. 1973, pp. 548-553; J. Removille et al.: "Zerstorungsfreie Untersuchung des Brennelementbundels eines Schnellbruterreaktors" *p. 552*.

Primary Examiner—Harvey E. Behrend
Attorney, Agent, or Firm—Oblon, Fisher, Spivak, McClelland & Maier

[57] ABSTRACT

A device for detecting fissionable material including a neutron source, two parallelepipedal panels placed on a support and forming a dihedral with an adjustable opening. The dihedral has an edge centered on the neutron source, and the panels consist of solid modules made of a material able to thermalize the neutrons and of a module of the same material in which a unit for detecting fission neutrons is housed. This detection unit is located at the end opposite the neutron source, and the object to be checked is placed between the two panels. The device has application to the checking of nuclear waste.

3 Claims, 2 Drawing Figures

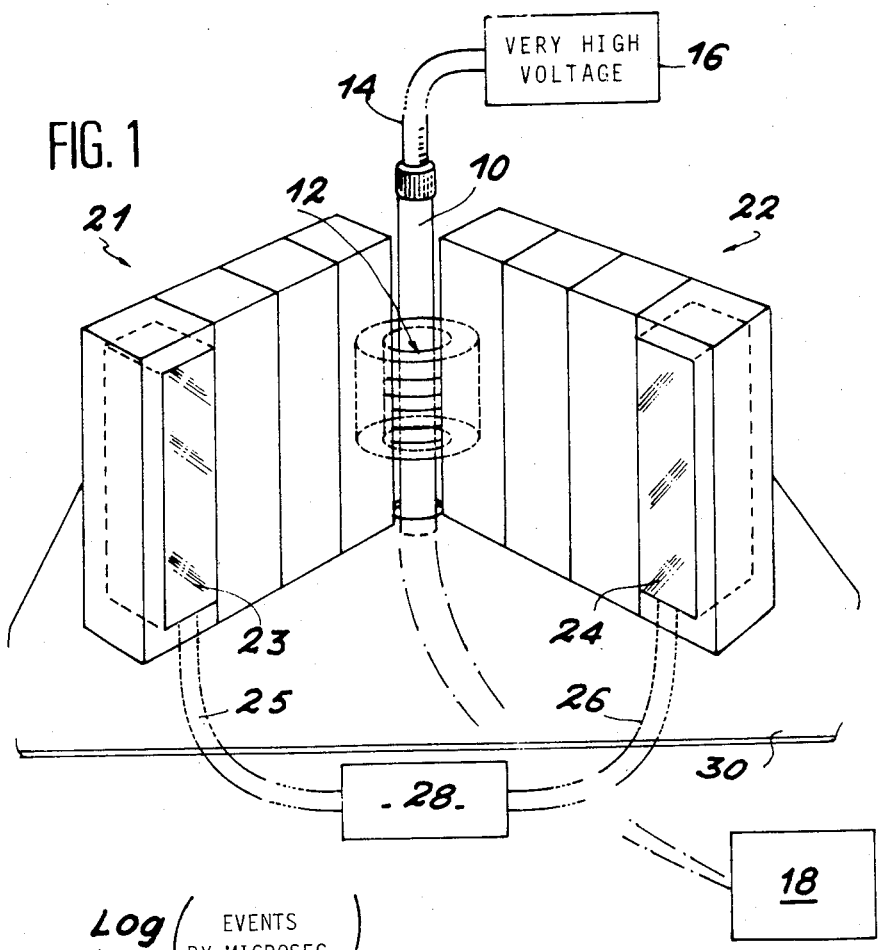
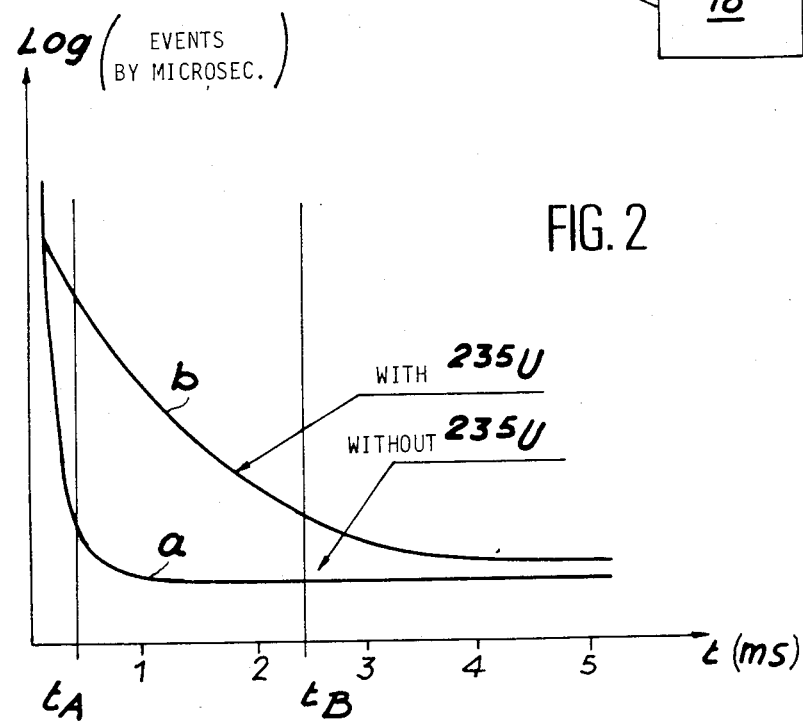

DEVICE FOR DETECTING FISSIONABLE MATERIAL

BACKGROUND OF THE INVENTION

1. Field of the Invention

This invention relates to a device for detecting fissionable material.

2. Discussion of the Background

To check the presence of fissionable material, particularly in nuclear waste, it is known that it is possible to use thermal neutrons produced from a source associated with thermalization means, these thermal neutrons being able to produce fission neutrons in the material to be checked, if it contains fissionable material. Detection of the latter then is equivalent to detection of fission neutrons.

SUMMARY OF THE INVENTION

This invention has as its object a device which puts this process into practice. The originality of the invention resides in the simplicity of the means used, a simplicity which leads to an easy use of the device.

Specifically, the device of the invention comprises two parallelepipedal panels placed on a support and forming a dihedral with an adjustable opening, this dihedral having an edge centered on a neutron source, these panels consisting of solid modules made of a material able to thermalize the neutrons and of a module of the same material in which a unit for detecting fission neutrons is housed, this detection unit being located at the end opposite the neutron source.

In this way, there is obtained a lightweight device of slight bulk and which is therefore easily transportable and adaptable to the products to be checked.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 shows diagrammatically the device of the invention,

FIG. 2 is a graph showing distribution over time of the events detected with and without fissionable material.

DESCRIPTION OF THE PREFERRED EMBODIMENTS

Referring now to the drawings, wherein like reference numerals designate identical or corresponding parts throughout the several views, the device shown in FIG. 1 comprises a pulsed neutron generator 10 of 14 MeV, surrounded by a lead converter unit 12. This generator, which is of a known type, consists of an elongated cylindrical envelope inside of which is a target of tritiated titanium. In a particular embodiment, the assembly forms a cylinder 7 cm in diameter and 74 cm long. This generator is connected on one side by a wire 14 to a very high voltage power supply 16, and on the other side by a wire 17 to an electronic box 18. The wires can be more than ten meters long. The assembly can be remote controlled.

Converter 12 is a lead cylinder about 15 cm in height and 5 cm thick. It is placed around the cylindrical generator at the level of the target producing the neutrons.

The generator-converter assembly is placed on the edge of the dihedral formed by two panels 21 and 22. These panels each consist, in the embodiment shown, of four polyethylene modules. Three modules are solid. The fourth is hollowed and makes it house a detection unit, respectively 23 and 24. These units 23, 24 each consist of three $^3$He counters (of the 65NH45 type) surrounded with cadmium and $B_4C$. These six counters are connected by wires 25 and 26 to an electronic circuit 28.

Panels 21 and 22 rest on a support 30 and form any adjustable angle, for example 120°. The object to be checked is placed between the two panels, in the vicinity of the detection units. The smaller the angle formed by the panels, the better is the sensitivity.

FIG. 2 makes it possible to understand the principle of detecting a fissionable element. The curves represent variations over time, laid off as abscissas, of the number of events detected during a certain interval of time (for example, 10 microseconds). This number is laid off as ordinates, in logarithmic scale. If there is no fissionable element in the material checked, the number of events detected by units 23 and 24 decreases very rapidly after the instant corresponding to the emission of the burst of neutrons by the generator (an instant taken as origin of the times). The development is represented by curve a. After a time $t_A$, the neutrons slowed by the polyethylene are found with an energy less than the detection threshold.

When a fissionable material like $^{235}U$ is present in the checked material, the development is different: the thermal neutrons present after instant $t_A$ can produce prompt fission neutrons which are detected by the detection units. Hence, a curve b which differs considerably from curve a results. A counting interval between instants $t_A$ and $t_B$ is then defined. This interval is a few milliseconds (for example 2). The result of the counting in this interval is either slight (no fissionable material), or strong (presence of fissionable material). The role of circuit 28 is to perform this counting. For this purpose, it comprises a preamplifier, an amplifier and a discriminator (none of which are shown) delivering logic pulses. A monostable multivibrator (not shown) of time $t_A$ controlled by the emission of neutrons opens a counting gate at instant $t_A$ which follows the emission of the burst of neutrons. A monostable multivibrator of time $t_B$ closes this gate. Between these two instants, the detected events are counted.

A multichannel analyzer operating in multiscale can also be used.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. Device for detecting fissionable material, comprising:

a converter unit;

a source of thermal neutrons surrounded by said converter unit;

means for thermalizing neutrons emitted by said source of thermal neutrons, such that thermalized neutrons emitted by said source of thermal neutrons interact with an object to be checked to cause said object to emit fission neutrons if said object contains fissionable material;

a detection assembly insensitive to thermal neutrons but sensitive to fission neutrons, said detection assembly placed in the vicinity of where the object to be checked is located;

two parallelepipedal panels placed on a support and forming a dihedral having an adjustable opening, said dihedral having an edge centered on the source of thermal neutrons, said panels each comprising solid modules made of a material able to thermalize the neutrons emitted by said source and an end module of the same material as said solid modules;

said detection assembly comprising fission neutron detectors housed in respective of said end modules which are located at respective ends of said panels opposite the neutron source, the object to be checked being placed between said two panels.

2. Device according to claim 1, wherein the modules of the panels are made of polyethylene.

3. Device according to claim 1, wherein the detecting means housed in each end module comprises $^3$He counters.

* * * * *